US011827918B2

(12) United States Patent
Berryman et al.

(10) Patent No.: US 11,827,918 B2
(45) Date of Patent: *Nov. 28, 2023

(54) REPEATED FED-BATCH CULTURE METHODS

(71) Applicant: Mara Renewables Corporation, Dartmouth (CA)

(72) Inventors: Kevin Berryman, Dartmouth (CA); Zhiyong Sun, Dartmouth (CA); Michael Milway, Dartmouth (CA); Mercia Valentine, Dartmouth (CA); Roberto E. Armenta, Dartmouth (CA)

(73) Assignee: MARA RENEWABLES CORPORATION, Dartmouth (CA)

( * ) Notice: Subject to any disclaimer, the term of this patent is extended or adjusted under 35 U.S.C. 154(b) by 118 days.

This patent is subject to a terminal disclaimer.

(21) Appl. No.: 17/139,817

(22) Filed: Dec. 31, 2020

(65) Prior Publication Data
US 2021/0123083 A1 Apr. 29, 2021

Related U.S. Application Data

(63) Continuation of application No. 14/882,742, filed on Oct. 14, 2015, now Pat. No. 10,920,261.

(60) Provisional application No. 62/064,694, filed on Oct. 16, 2014.

(51) Int. Cl.
C12Q 1/06 (2006.01)
C12N 1/04 (2006.01)
C12P 7/6409 (2022.01)
C12N 1/10 (2006.01)
C12P 7/6427 (2022.01)

(52) U.S. Cl.
CPC ............ *C12Q 1/06* (2013.01); *C12N 1/04* (2013.01); *C12N 1/10* (2013.01); *C12P 7/6409* (2013.01); *C12P 7/6427* (2013.01)

(58) Field of Classification Search
None
See application file for complete search history.

(56) References Cited

U.S. PATENT DOCUMENTS

| | | | |
|---|---|---|---|
| 5,340,594 | A | 8/1994 | Barclay |
| 5,340,742 | A | 8/1994 | Barclay |
| 6,607,900 | B2 | 8/2003 | Bailey et al. |
| 8,163,515 | B2 | 4/2012 | Burja et al. |
| 2001/0046691 | A1 | 11/2001 | Bailey et al. |
| 2007/0015263 | A1 | 1/2007 | Wumpelmann |
| 2009/0117194 | A1 | 5/2009 | Burja et al. |
| 2010/0124583 | A1 | 5/2010 | Medoff |
| 2011/0306102 | A1 | 12/2011 | Ratnam et al. |
| 2012/0244584 | A1 | 9/2012 | Zhang et al. |

FOREIGN PATENT DOCUMENTS

| | | |
|---|---|---|
| CN | 101981201 A | 2/2011 |
| CN | 102333880 | 1/2012 |
| CN | 103436561 | 12/2013 |
| CN | 101932696 | 3/2014 |
| JP | 2008541779 | 11/2008 |
| WO | 2009077054 | 6/2009 |
| WO | 2010097809 | 9/2010 |
| WO | 2011011660 | 1/2011 |
| WO | 2013146540 | 10/2013 |

OTHER PUBLICATIONS

Matsudo et al. "Repeated fed-batch cultivation of Arthrospira (Spirulina) platensis using urea as nitrogen source" (2009), Biochem Engineer J, vol. 43: 52-57 (Year: 2009).*
"Klebsiella Pneumoniae", Chinese Doctoral Dissertations Full-text Database Engineering Science and Technology I, Dec. 15, 2011, 17 pages.
U.S. Appl. No. 14/882,742, Advisory Action, dated Oct. 23, 2019, 3 pages.
U.S. Appl. No. 14/882,742, Final Office Action, dated Jun. 13, 2019, 11 pages.
U.S. Appl. No. 14/882,742, Final Office Action, dated Jan. 12, 2018, 14 pages.
U.S. Appl. No. 14/882,742, Non Final Office Action, dated Jan. 8, 2019, 11 pages.
U.S. Appl. No. 14/882,742, Non-Final Office Action, dated May 19, 2017, 11 pages.
U.S. Appl. No. 14/882,742, Non-Final Office Action, dated Jun. 16, 2020, 14 pages.
U.S. Appl. No. 14/882,742, "Restriction Requirement", dated Dec. 16, 2016, 7 pages.
AU2015332095, "First Examination Report", dated Sep. 9, 2020, 5 pages.
Application No. BR1120170035588, Office Action, dated Dec. 24, 2019, 7 pages.
Burja et al., "Isolation and Characterization of Polyunsaturated Fatty Acid producing Thraustochytrium Species: Screening of Strains and Optimization of Omega-3 Production", Applied Microbiology and Biotechnology, vol. 72, No. 6, 2006, pp. 1161-1169.
Application No. CA2,960,450, Office Action, dated Apr. 1, 2021, 3 pages.

(Continued)

Primary Examiner — Teresa E Knight
(74) Attorney, Agent, or Firm — Kilpatrick Townsend & Stockton LLP

(57) ABSTRACT

Provided herein are methods of culturing a microorganism. The method includes providing a container comprising one or more microorganisms and medium, wherein the microorganisms and medium form a start volume. The microorganisms and medium are cultured until the culture reaches a threshold indicator, wherein culturing comprises feeding one or more carbon sources to the culture and wherein the culture is at a threshold volume when the threshold indicator is reached. The method also includes harvesting a portion of the threshold volume to leave a residual volume that is 40% or less of the start volume and adding fresh medium to the container in an amount to return the volume of the culture to the start volume.

22 Claims, 3 Drawing Sheets

Specification includes a Sequence Listing.

(56) References Cited

OTHER PUBLICATIONS

Application No. CA2,960,450, Office Action, dated Feb. 20, 2020, 5 pages.
Chang et al., "Improvement of Docosahexaenoic Acid Production on Glycerol by *Schizochytrium* Sp. S31 with Constantly High Oxygen Transfer Coefficient", Bioresource Technology, vol. 142, 2013, pp. 400-406.
Chunsheng et al., "Optimization of Inoculum Draw-Off Volume for Repeated Fed-Batch Fermentation Process", Biotechnology and Bioengineering, vol. 34, 1989, pp. 117-120.
Application No. CL201700892, Office Action, dated Apr. 17, 2019, 12 pages.
Application No. CL201700892, Office Action, dated Nov. 28, 2018, 30 pages.
Application No. CN201580045701.X, Office Action, dated Sep. 3, 2020, 5 pages.
Application No. CN201580045701.X, Office Action, dated Feb. 3, 2020, 8 pages.
Application No. EP15850374.8, Extended European Search Report, dated May 4, 2018, 11 pages.
Application No. EP15850374.8, Office Action, dated May 28, 2019, 6 pages.
Ganuza et al., "High-Cell-Density Caultivation of *Schizochytrium* Sp. In an Ammonium/Ph-Auxostat Fed-Batch System", Biotechnol Lett, vol. 30, No. 9, 2008, pp. 1559-1564.
Hekmat et al., "Optimization of the Microbial Synthesis of Dihydroxyacetone from Glycerol with Gluconobacter Oxydans", Bioprocess and Biosystems Engineering, vol. 26, 2003, pp. 109-116.
Hekmat et al., "Optimization of the Microbial Synthesis of Dihydroxyacetone in a Semi-Continuous Repeated-Fed-Batch Process by in Situ Immobilization of Gluconobacter Oxydans", Process Biochemistry, vol. 42, No. 1, Jan. 2007, pp. 71-76.
Application No. IL250269, Office Action, dated Dec. 24, 2019, 7 pages.
IN201717003900, "First Examination Report", dated Jan. 27, 2021, 7 pages.
Ji et al., "Efficient Arachidonic Acid-Rich Oil Production by Mortierella Alpina through a Repeated Fed-Batch Fermentation Strategy", Bioresource Technology, vol. 170, Aug. 1, 2014, pp. 356-360.
Application No. JP2017-512942, Office Action, dated May 12, 2020, 5 pages.
Application No. JP2017-512942, Office Action, dated Jul. 9, 2019, 7 pages.
Application No. MX/A/2017/002150, Office Action, dated Jun. 11, 2020.
Application No. PCT/IB2015/057808, International Preliminary Report on Patentability, dated Apr. 27, 2017, 6 pages.
Application No. PCT/IB2015/057808, International Search Report and Written Opinion, dated Dec. 24, 2015, 8 pages.
Qu et al., "Batch, Fed-Batch and Repeated Fed-Batch Fermentation Processes of the Marine Thraustochytrid *Schizochytrium* Sp. For Producing Docosahexaenoic Acid", Bioprocess and Biosystems Engineering, vol. 36, No. 12, May 15, 2013, pp. 1905-1912.
Qu et al., "Enhancement of Docosahexaenoic Acid Production by *Schizochytrium* sp. Using a Two-Stage Oxygen Supply Control Strategy Based on Oxygen Transfer Coefficient", Letters in Applied Microbiology, vol. 52, No. 1, 2010, pp. 22-27.
Yokochi et al., "Optimization of Docosahexaenoic Acid Productions by Schizochytrium Limacinum SR21", Applied Microbiology and Biotechnology, vol. 49, Issue 1, Jan. 1998, pp. 72-76.
Zhao et al., "Lipid Production by Rhodosporidium Toruloides Y4 Using Different Substrate Feeding Strategies", Journal of Industrial Microbiology and Biotechnology, vol. 38, No. 5, May 2011, pp. 627-632.
CA2,960,450, "Office Action", dated Mar. 2, 2022, 3 pages.
CN202110216510.2, "Office Action", dated Jul. 20, 2022, 7 pages.
KR2017-7008993, "Office Action", dated Jul. 26, 2022, 10 pages.
KR2017-7008993, "Office Action", dated Jan. 25, 2022, 7 pages.
AU2021202832, "Second Examination Report", dated May 11, 2023, 4 pages.
BR1120170035588, "Office Action", dated May 2, 2023, 5 pages.
CN202110216510.2, "Office Action", dated Mar. 15, 2023, 4 pages.
AU2021202832, "First Examination Report", dated Nov. 21, 2022, 5 pages.

* cited by examiner

SEQUENCE LISTING

```
<160> NUMBER OF SEQ ID NOS: 1

<210> SEQ ID NO 1
<211> LENGTH: 1723
<212> TYPE: DNA
<213> ORGANISM: Artificial Sequence
<220> FEATURE:
<223> OTHER INFORMATION: Synthetic Construct

<400> SEQUENCE: 1
gtagtcatac gctcgtctca aagattaagc catgcatgtg taagtataag cgattatact      60
gtgagactgc gaacggctca ttatatcagt tatgatttct tcggtatttt ctttatatgg     120
atacctgcag taattctgga attaatacat gctgagaggg cccgactgtt cgggagggcc     180
gcacttatta gagttgaagc caagtaagat ggtgagtcat gataattgag cagatcgctt     240
gtttggagcg atgaatcgtt tgagtttctg ccccatcagt tgtcgacggt agtgtattgg     300
actacggtga ctataacggg tgacggggag ttagggctcg actccggaga gggagcctga     360
gagacggcta ccacatccaa ggaaggcagc aggcgcgtaa attacccaat gtggactcca     420
cgaggtagtg acgagaaata tcaatgcggg gcgcttcgcg tcttgctatt ggaatgagag     480
caatgtaaaa ccctcatcga ggatcaactg gagggcaagt ctggtgccag cagccgcggt     540
aattccagct ccagaagcgt atgctaaagt tgttgcagtt aaaaagctcg tagttgaatt     600
tctggggcgg gagccccggt ctttgcgcga ctgcgctctg tttgccgagc ggctcctctg     660
ccatcctcgc ctcttttttt agtggcgtcg ttcactgtaa ttaaagcaga gtgttccaag     720
caggtcgtat gacctggatg tttattatgg gatgatcaga tagggctcgg gtgctatttt     780
gttggtttgc acatctgagt aatgatgaat aggaacagtt gggggtattc gtatttagga     840
gctagaggtg aaattcttgg atttccgaaa gacgaactac agcgaaggca tttaccaagc     900 atgtttcat taatcaagaa cgaaagtctg gggatcgaag atgattagat accatcgtag     960
tctagaccgt aaacgatgcc gacttgcgat tgcggggtgt ttgtattgga ccctcgcagc    1020
agcacatgag aaatcaaagt ctttgggttc cgggggagt atggtcgcaa ggctgaaact    1080
taaaggaatt gacggaaggg caccaccagg agtggagcct gcggcttaat ttgactcaac    1140
acgggaaaac ttaccaggtc cagacatagg taggattgac agattgagag ctctttcttg    1200
attctatggg tggtggtgca tggccgttct tagttggtgg agtgatttgt ctggttaatt    1260
ccgttaacga acgagacctc ggcctactaa atagcggtgg gtatggcgac atacttgcgt    1320
acgcttctta gagggacatg ttcggtatac gagcaggaag ttcgaggcaa taacaggtct    1380
```

-continued

```
gtgatgccct tagatgttct gggccgcacg cgcgctacac tgatgggttc aacgggtggt    1440
catcgttgtt cgcagcgagg tgctttgccg gaaggcatgg caaatccttt caacgcccat    1500
cgtgctgggg ctagattttt gcaattatta atctccaacg aggaattcct agtaaacgca    1560
agtcatcagc ttgcattgaa tacgtccctg ccctttgtac acaccgcccg tcgcacctac    1620
cgattgaacg gtccgatgaa accatgggat gaccttttga gcgtttgttc gcgagggggg    1680
tcagaactcg ggtgaatctt attgtttaga ggaaggtgaa gtc                     1723
```

REPEATED FED-BATCH CULTURE METHODS

CROSS-REFERENCE TO RELATED APPLICATION

This application is a continuation of U.S. patent application Ser. No. 14/882,742, filed Oct. 14, 2015, which claims priority to U.S. Provisional Application No. 62/064,694, filed Oct. 16, 2014, both of which are incorporated herein by reference in their entireties.

BACKGROUND OF THE INVENTION

Heterotrophic fermentations of microorganisms including *Thraustochytrid* species are efficient ways of generating high value oil and biomass products. Under certain cultivation conditions, microorganisms synthesize intracellular oil, which can be extracted and used to produce biofuel (biodiesel, bio-jetfuel, and the like) and nutritional lipids (polyunsaturated fatty acids, e.g. DHA, EPA, DPA). The biomass of microorganisms such as *Thraustochytrid* species is also of great nutritional value due to the high PUFA and protein content and can be used as nutritional supplement for animal feed.

Microorganism fermentation processes are carried out mostly in batch or fed-batch processes. Batch processes typically involve a closed system culture in which cells are grown in a fixed volume of nutrient culture medium under specific conditions (e.g., specific levels of nutrients, temperature, pressure, and the like) to a certain density in a fermenter, harvested and processed as a batch. In typical fed-batch processes, one or more nutrients are fed or supplied to a fermenter, in which they remain until the end of the culture process. Fed-batch culture processes can be superior to batch culture processes when controlling concentrations of a nutrient (or nutrients) affects the yield or activity of a desired product. Oil-producing fermentation processes are typically comprised of two cultivation stages, a cell proliferation stage, during which all necessary nutrients are available for unlimited culture growth, followed by an oil accumulation stage, during which a key growth nutrient (typically nitrogen) is purposely limited in the medium while excessive carbon nutrient is provided and channeled into oil synthesis. When the target cell concentration and oil content is reached, the fermentation process is stopped and oil-rich biomass is harvested. The fermenter vessel then must be cleaned, sterilized and re-batched with fresh medium, and a seed train needs to be ready to inoculate the production vessel again (e.g., a "turnaround" operation between batch/fed-batch fermentations). Such a turnaround operation is often time and energy consuming and limits the total available operating hours of the production vessel for an established production process. Alternatively, microorganisms can be cultured using continuous methods where fresh medium is continuously added to the fermenter, while culture liquid is continuously removed to keep the culture volume constant. Continuous culture processes can be used to maintain the microorganism at a specific growth rate or physiological steady state but can be difficult to maintain without disruption and are typically used for research purposes, as fed-batch or batch cultures tend to provide better results (e.g., higher oil yield) and are easier to use for large scale production purposes.

BRIEF SUMMARY OF THE INVENTION

Provided herein are methods of culturing a microorganism. The methods include providing a container comprising one or more microorganisms and medium, wherein the microorganisms and medium form a start volume, culturing the microorganisms in the medium until the culture reaches a threshold indicator, wherein culturing comprises feeding one or more carbon sources to the culture and wherein the culture is at a threshold volume when the threshold indicator is reached, harvesting a portion of the threshold volume to leave a residual volume that is 40% or less of the start volume, and adding fresh medium to the container in an amount to return the volume of the culture to the start volume.

DETAILED DESCRIPTION OF THE INVENTION

Figure 1:
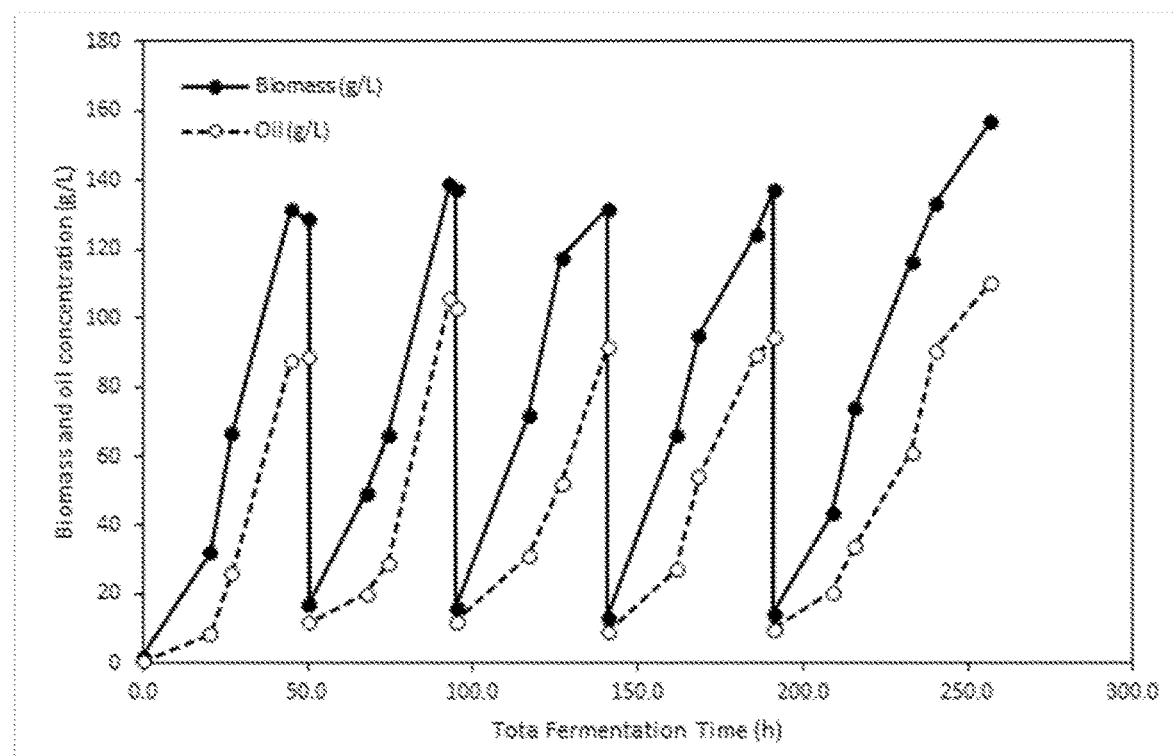
FIG. 1 is a graph showing the progression of in-vessel biomass concentration and oil concentration over time during a repeated fed-batch fermentation in a 30 L fermenter.

Methods of cultivating microorganisms and methods of producing oil by a repeated fed-batch process are provided herein. The provided methods result in greater overall volumetric productivity of both biomass and oil than a typical batch or fed-batch process. Briefly, the process involves cultivating microorganisms in a fed-batch method where, upon completion of the fermentation as defined by reaching a particular volume and/or by meeting volumetric biomass and oil yields, the vessel is drained in a manner which maintains its sterility and leaves behind a certain predetermined volume of culture (e.g., 10% of the initial media volume). Fresh, sterile media is then added to the vessel where the culture left behind from the previous fermentation is used as a seed. This process can be repeated indefinitely. The amount of culture left behind for use as a seed can vary; however, one should consider the tradeoff between biomass left un-harvested, and the reduced time spent in the lag-phase of the subsequent fermentation. In using a repeated fed-batch process, fermenter turnaround time is significantly reduced which, in turn, leads to higher overall volumetric productivity of biomass and oil; far exceeding that of conventional batch and fed-batch processes. Also, the repeated fed-batch process minimizes the need for cleaning and sterilization, thereby lowering operating costs. Furthermore, there is less dependence on a seed train, which reduces both labor and energy costs.

Microorganisms

The methods described herein include extracting lipids from a population of microorganisms. The population of microorganisms described herein can be algae (e.g., microalgae), fungi (including yeast), bacteria, or protists. Optionally, the microorganism includes Thraustochytrids of the order Thraustochytriales, and, more specifically, Thraustochytriales of the genus *Thraustochytrium*. Optionally, the population of microorganisms includes Thraustochytriales as described in U.S. Pat. Nos. 5,340,594 and 5,340,742, which are incorporated herein by reference in their entireties. The microorganism can be a *Thraustochytrium* species, such as the *Thraustochytrium* species deposited as ATCC Accession No. PTA-6245 (i.e., ONC-T18) as described in U.S. Pat. No. 8,163,515, which is incorporated by reference herein in its entirety. Thus, the microorganism can have an 18s rRNA sequence that is at least 95%, 96%, 97%, 98%, 99%, 99.1%, 99.2%, 99.3%, 99.4%, 99.5%, 99.6%, 99.7%, 99.8%, 99.9% or more (e.g., including 100%) identical to SEQ ID NO:1.

The microorganisms for use in the methods described herein can produce a variety of lipid compounds. As used herein, the term lipid includes phospholipids, free fatty acids, esters of fatty acids, triacylglycerols, sterols and sterol esters, carotenoids, xanthophyls (e.g., oxycarotenoids), hydrocarbons, and other lipids known to one of ordinary skill in the art. Optionally, the lipid compounds include unsaturated lipids. The unsaturated lipids can include polyunsaturated lipids (i.e., lipids containing at least 2 unsaturated carbon-carbon bonds, e.g., double bonds) or highly unsaturated lipids (i.e., lipids containing 4 or more unsaturated carbon-carbon bonds). Examples of unsaturated lipids include omega-3 and/or omega-6 polyunsaturated fatty acids, such as docosahexaenoic acid (i.e., DHA), eicosapentaenoic acid (i.e., EPA), and other naturally occurring unsaturated, polyunsaturated and highly unsaturated compounds.

Processes

Provided herein is a method of culturing a microorganism. The method includes providing a container comprising one or more microorganisms and medium, wherein the microorganisms and medium form a start volume; culturing the microorganisms in the medium until the culture reaches a threshold indicator, wherein culturing comprises feeding one or more carbon sources to the culture and wherein the culture is at a threshold volume when the threshold indicator is reached; harvesting a portion of the threshold volume to leave a residual volume that is 40% or less of the start volume; and adding fresh medium to the container in an amount to return the volume of the culture to the start volume.

The methods are applicable to large-scale fermentation as well as small-scale fermentation and any fermentation scale between. Large-scale fermentation, as used herein, refers to fermentation in a fermenter that is at least approximately 1,000 L in volumetric capacity (i.e., working volume), leaving adequate room for headspace. Small-scale fermentation refers generally to fermentation in a fermenter that is generally no more than approximately 100 L in volumetric capacity, such as 5 L, 10 L, 50 L or 100 L. A demonstrated advantage of the present fed-batch fermentation process is that it may be utilized for the production of oil at the 5-10 L fermenter scale and is scalable to any volume, for example, 100 L, 150 L, 250 L, 500 L, 1000 L or more, without limitation.

As described in more detail in the examples below, the repeated fed-batch process alleviates, if not eliminates, the turnaround time of the production vessel, with the ultimate goal of increasing volumetric productivity. An example of how volumetric productivity increases over that of typical fed batch fermentation is illustrated in FIG. 1. Assuming a 24 hour turnaround time for the production vessel to be included in the total process time the overall biomass (X) productivity at any given time can be calculated as: X (gram)/Vessel Working Volume (L)/Time*24 (hours/day) with the final unit being g/L-day. Oil productivity can be calculated in a similar manner as: Oil (g)/Vessel Working Volume (L)/Time*24 (hours/day). As seen in FIG. 1 biomass and oil productivities of a fed-batch process will remain constant over time. Conversely, after the first cycle of the repeated fed-batch process average productivity increases, far exceeding that of the fed-batch process as turnaround time is not required, and cycle time is decreased due to increased seed density, in this dataset a 20% seed was employed.

In the provided methods, the residual volume can be from 1% to 40% of the start volume, e.g., from 1% to 5%, 1% to 10%, 1% to 20%, 1% to 30%, 5% to 10%, 5% to 20%, 5% to 30%, 10%, to 20%, 10% to 30%, 20% to 40%, or any volume between 1% and 40% inclusive of the start volume. Optionally, the residual volume is at least about 10% of the start volume.

The provided methods include culturing the microorganisms until the culture reaches a threshold indicator for a parameter. As used herein, the term parameter refers to a variable in the culture conditions which can be monitored and controlled to adjust the progress of a microorganism culture. A threshold indicator is a preselected level or concentration for a given parameter. Such parameters include, but are not limited to, volume of the culture, optical density (OD), cell concentration, carbon dioxide production rate, pH, dissolved oxygen (DO), time, concentration of nutrient in culture medium, accumulation of metabolic by-products, temperature, biomass productivity, and oil productivity. Any suitable parameter or combination of parameters is contemplated for use as would be understood by a person of ordinary skill in the art and based upon the guidance provided herein. Optionally, the threshold indicator is a preselected level or concentration of nutrient(s) in the culture medium. Suitable nutrients that can be measured in the culture medium include, but are not limited to, carbon and nitrogen.

The provided methods optionally include repeating the steps of (i) culturing the microorganisms in the medium until the culture reaches a threshold indicator, wherein culturing comprises feeding one or more carbon sources to the culture and wherein the culture is at a threshold volume when the threshold indicator is reached; (ii) harvesting a portion of the threshold volume to leave a residual volume that is 40% or less of the start volume; and (iii) adding fresh medium to the container in an amount to return the volume of the culture to the start volume. Optionally, the steps are repeated two or more times. Optionally, the steps are repeated 2, 3, 4, 5, 6, 7, 8, 9, or 10 times. When the process is repeated multiple times, as discussed above, the start volume and the residual volumes can vary each time or each round. Optionally, the start volumes and residual volumes can remain the same each time or each round. By way of example, in a first round, the residual volume can be 2% of the start volume and in successive rounds, the residual volume can be 10% of the start volume. The residual volume in the successive rounds can also vary, e.g., it can be 10% of the start volume in one round and 20% of the start volume in another round. The provided methods advantageously allow for the culture to be maintained over a long period of time. As such, the method steps can be repeated as long as it is desired to maintain the culture and continue to harvest a portion for further use.

Optionally, the culture is maintained for a period of hours, days, weeks or months. Optionally, the culture is maintained for at least 150 to 500 hours. For example, the culture can be maintained for at least 250 hours. Optionally, the culture is maintained for one, two, three, four, or five weeks.

Optionally, the provided methods include production of a single or only one seed or seed train. Typical fed-batch cultivation of microorganisms requires production of a seed culture produced in a step-wise manner called a seed train. The seed train serves to build up the volume and density of a culture to inoculate a clean and sterile production vessel. A seed train requires time, energy for sterilization, and also creates more opportunity for contamination as the culture is transferred between multiple vessels. The repeated fed-batch method requires this seed train only to inoculate the first cycle. Likewise, the production vessel only needs to be sterilized for the initial cycle. Therefore, time is saved in turning around the production vessel (cleaning and sterilization) and energy is saved from cleaning, sterilizing and operating vessels in the seed train. Thus, the provided methods optionally include a single sterilization step. Moreover, risk of contamination is alleviated from culture transfers in the seed train for sequential batches. Thus, the provided methods result in reduced contamination as compared to typical batch or fed-batch processes.

Using the production vessel culture (i.e., the residual volume) as the seed for successive batches also allows the choice of selecting the percentage of seed to use without requiring purchase of larger equipment or additional fermenters in the seed train. For example, a 2% seed volume (2000 L for a 100,000 L start volume in a 200,000 L working volume production vessel) could be used for the initial batch fermentation, whereas all following iterations could be inoculated with a 10% seed. A 2% seed culture eliminates the need for a larger vessel in the seed train (i.e., a 10,000 L working volume vessel) alleviating capital costs/investment and lowering risk of contamination as there is one less transfer of the seed culture. By using a 2% seed, the lag phase of microorganism growth is increased, leading to lower volumetric productivities in the production vessels. However, with successive batches using the repeated fed-batch method being inoculated with a 10% seed volume this long lag phase is dramatically shortened.

The provided methods include or can be used in conjunction with additional steps for culturing microorganisms according to methods known in the art. For example, a *Thraustochytrid*, e.g., a *Thraustochytrium* sp., can be cultivated according to methods described in U.S. Patent Publications 2009/0117194 or 2012/0244584, which are herein incorporated by reference in their entireties for each step of the methods or composition used therein.

Microorganisms are grown in a growth medium (also known as "culture medium"). Any of a variety of medium can be suitable for use in culturing the microorganisms described herein. Optionally, the medium supplies various nutritional components, including a carbon source and a nitrogen source, for the microorganism. Medium for *Thraustochytrid* culture can include any of a variety of carbon sources. Examples of carbon sources include fatty acids, lipids, glycerols, triglycerols, carbohydrates, polyols, amino sugars, and any kind of biomass or waste stream. Fatty acids include, for example, oleic acid. Carbohydrates include, but are not limited to, glucose, cellulose, hemicellulose, fructose, dextrose, xylose, lactulose, galactose, maltotriose, maltose, lactose, glycogen, gelatin, starch (corn or wheat), acetate, m-inositol (e.g., derived from corn steep liquor), galacturonic acid (e.g., derived from pectin), L-fucose (e.g., derived from galactose), gentiobiose, glucosamine, alpha-D-glucose-1-phosphate (e.g., derived from glucose), cellobiose, dextrin, alpha-cyclodextrin (e.g., derived from starch), and sucrose (e.g., from molasses). Polyols include, but are not limited to, maltitol, erythritol, and adonitol. Amino sugars include, but are not limited to, N-acetyl-D-galactosamine, N-acetyl-D-glucosamine, and N-acetyl-beta-D-mannosamine. Optionally, the carbon source is glucose. As noted above, in the provided methods, the carbon source is provided at a high concentration, e.g., at least 200 g/L.

Optionally, the microorganisms provided herein are cultivated under conditions that increase biomass and/or production of a compound of interest (e.g., oil or total fatty acid (TFA) content). Thraustochytrids, for example, are typically cultured in saline medium. Optionally, Thraustochytrids can be cultured in medium having a salt concentration from about 0.5 g/L to about 50.0 g/L. Optionally, Thraustochytrids are cultured in medium having a salt concentration from about 0.5 g/L to about 35 g/L (e.g., from about 18 g/L to about 35 g/L). Optionally, the Thraustochytrids described herein can be grown in low salt conditions. For example, the Thraustochytrids can be cultured in a medium having a salt concentration from about 0.5 g/L to about 20 g/L (e.g., from about 0.5 g/L to about 15 g/L). The culture medium optionally includes NaCl. Optionally, the medium includes natural or artificial sea salt and/or artificial seawater.

The culture medium can include non-chloride-containing sodium salts as a source of sodium. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein. A significant portion of the total sodium, for example, can be supplied by non-chloride salts such that less than about 100%, 75%, 50%, or 25% of the total sodium in culture medium is supplied by sodium chloride.

Optionally, the culture medium has chloride concentrations of less than about 3 g/L, 500 mg/L, 250 mg/L, or 120 mg/L. For example, culture medium for use in the provided methods can have chloride concentrations of between and including about 60 mg/L and 120 mg/L.

Medium for Thraustochytrids culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$)), peptone, tryptone, yeast extract, malt extract, fish meal, sodium glutamate, soy extract, casamino acids and distiller grains. Concentrations of nitrogen sources in suitable medium typically range between and including about 1 g/L and about 25 g/L.

The medium optionally includes a phosphate, such as potassium phosphate or sodium-phosphate. Inorganic salts and trace nutrients in medium can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium can be sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar or agarose) that provide structural support and/or allow the medium to be in solid form.

Cells can be cultivated over a period of time. Optionally, the cells are cultured for anywhere from 1 day to 60 days. Optionally, the culture is maintained for a period of hours, days, weeks or months. Optionally, the culture is maintained for at least 150 to 500 hours. Optionally, the culture is maintained for at least 250 hours. Optionally, the culture is maintained for one, two, three, four, or five weeks. Cultivation is optionally carried out at temperatures from about 4° C. to about 30° C., e.g., from about 18° C. to about 28° C. Cultivation can include aeration-shaking culture, shaking culture, stationary culture, batch culture, semi-continuous culture, continuous culture, rolling batch culture, wave culture, or the like. Cultivation can be performed using a conventional agitation-fermenter, a bubble column fermenter (batch or continuous cultures), an airlift fermenter, a wave fermenter, and the like.

Cultures can be aerated by one or more of a variety of methods, including shaking. Optionally, shaking ranges from about 100 rpm to about 1000 rpm, e.g., from about 350 rpm to about 600 rpm or from about 100 to about 450 rpm. Optionally, the cultures are aerated using different shaking speeds during biomass-producing phases and during lipid-producing phases. Alternatively or additionally, shaking speeds can vary depending on the type of culture vessel (e.g., shape or size of flask).

The production of desirable lipids can be enhanced by culturing cells according to methods that involve a shift of one or more culture conditions in order to obtain higher quantities of desirable compounds. Optionally, cells are cultured first under conditions that maximize biomass, followed by a shift of one or more culture conditions to conditions that favor lipid productivity. Conditions that are shifted can include oxygen concentration, C:N ratio, temperature, and combinations thereof. Optionally, a two-stage culture is performed in which a first stage favors biomass production (e.g., using conditions of high oxygen (e.g., generally or relative to the second stage), low C:N ratio, and ambient temperature), followed by a second stage that favors lipid production (e.g., in which oxygen is decreased, C:N ratio is increased, and temperature is decreased, as compared to the first stage). In contrast to previously described methods, the provided methods allow for maintaining the culture for a prolonged time under conditions at high levels of oil or lipid production.

Pasteurization

Optionally, the resulting biomass is pasteurized to inactivate undesirable substances present in the biomass. For example, the biomass can be pasteurized to inactivate compound degrading substances. The biomass can be present in the fermentation medium or isolated from the fermentation medium for the pasteurization step. The pasteurization step can be performed by heating the biomass and/or fermentation medium to an elevated temperature. For example, the biomass and/or fermentation medium can be heated to a temperature from about 50° C. to about 95° C. (e.g., from about 55° C. to about 90° C. or from about 65° C. to about 80° C.). Optionally, the biomass and/or fermentation medium can be heated from about 30 minutes to about 120 minutes (e.g., from about 45 minutes to about 90 minutes, or from about 55 minutes to about 75 minutes). The pasteurization can be performed using a suitable heating means, such as, for example, by direct steam injection.

Optionally, no pasteurization step is performed. Stated differently, the method taught herein optionally lacks a pasteurization step.

Harvesting and Washing

Optionally, the biomass can be harvested according to a variety of methods, including those currently known to one skilled in the art. For example, the biomass can be collected from the fermentation medium using, for example, centrifugation (e.g., with a solid-ejecting centrifuge) or filtration (e.g., cross-flow filtration). Optionally, the harvesting step includes use of a precipitation agent for the accelerated collection of cellular biomass (e.g., sodium phosphate or calcium chloride).

Optionally, the biomass is washed with water. Optionally, the biomass can be concentrated up to about 20% solids. For example, the biomass can be concentrated to about 5% to about 20% solids, from about 7.5% to about 15% solids, or from about solids to about 20% solids, or any percentage within the recited ranges. Optionally, the biomass can be concentrated to about 20% solids or less, about 19% solids or less, about 18% solids or less, about 17% solids or less, about 16% solids or less, about 15% solids or less, about 14% solids or less, about 13% solids or less, about 12% solids or less, about 11% solids or less, about 10% solids or less, about 9% solids or less, about 8% solids or less, about 7% solids or less, about 6% solids or less, about 5% solids or less, about 4% solids or less, about 3% solids or less, about 2% solids or less, or about 1% solids or less.

Isolation and Extraction

The provided methods, optionally, include isolating the polyunsaturated fatty acids from the biomass or microorganisms. Isolation of the polyunsaturated fatty acids can be performed using one or more of a variety of methods, including those currently known to one of skill in the art. For example, methods of isolating polyunsaturated fatty acids are described in U.S. Pat. No. 8,163,515, which is incorporated by reference herein in its entirety. Optionally, the medium is not sterilized prior to isolation of the polyunsaturated fatty acids. Optionally, sterilization comprises an increase in temperature. Optionally, the polyunsaturated fatty acids produced by the microorganisms and isolated from the provided methods are medium chain fatty acids. Optionally, the one or more polyunsaturated fatty acids are selected from the group consisting of alpha linolenic acid, arachidonic acid, docosahexaenoic acid, docosapentaenoic acid, eicosapentaenoic acid, gamma-linolenic acid, linoleic acid, linolenic acid, and combinations thereof.

Products

Oil including polyunsaturated fatty acids (PUFAs) and other lipids produced according to the method described herein can be utilized in any of a variety of applications exploiting their biological, nutritional, or chemical properties. Thus, the provided methods optionally include isolating oil from the harvested portion of the threshold volume. Optionally, the oil is used to produce fuel, e.g., biofuel. Optionally, the oil can be used in pharmaceuticals, food supplements, animal feed additives, cosmetics, and the like. Lipids produced according to the methods described herein can also be used as intermediates in the production of other compounds.

By way of example, the oil produced by the microorganisms cultured using the provided methods can comprise fatty acids. Optionally, the fatty acids are selected from the group consisting of alpha linolenic acid, arachidonic acid, docosahexaenoic acid, docosapentaenoic acid, eicosapentaenoic acid, gamma-linolenic acid, linoleic acid, linolenic acid, and combinations thereof. Optionally, the oil comprises triglycerides. Optionally, the oil comprises fatty acids selected from the group consisting of palmitic acid (C16:0), myristic acid (C14:0), palmitoleic acid (C16:1(n-7)), cis-vaccenic acid (C18:1(n-7)), docosapentaenoic acid (C22:5(n-6)), docosahexaenoic acid (C22:6(n-3)), and combinations thereof.

Optionally, the lipids produced according to the methods described herein can be incorporated into a final product (e.g., a food or feed supplement, an infant formula, a pharmaceutical, a fuel, etc.) Suitable food or feed supplements into which the lipids can be incorporated include beverages such as milk, water, sports drinks, energy drinks, teas, and juices; confections such as candies, jellies, and biscuits; fat-containing foods and beverages such as dairy products; processed food products such as soft rice (or porridge); infant formulae; breakfast cereals; or the like. Optionally, one or more produced lipids can be incorporated into a dietary supplement, such as, for example, a vitamin or multivitamin. Optionally, a lipid produced according to the method described herein can be included in a dietary supplement and optionally can be directly incorporated into a component of food or feed (e.g., a food supplement).

Examples of feedstuffs into which lipids produced by the methods described herein can be incorporated include pet foods such as cat foods; dog foods and the like; feeds for aquarium fish, cultured fish or crustaceans, etc.; feed for farm-raised animals (including livestock and fish or crustaceans raised in aquaculture). Food or feed material into which the lipids produced according to the methods described herein can be incorporated is preferably palatable to the organism which is the intended recipient. This food or feed material can have any physical properties currently known for a food material (e.g., solid, liquid, soft).

Optionally, one or more of the produced compounds (e.g., PUFAs) can be incorporated into a nutraceutical or pharmaceutical. Examples of such a nutraceuticals or pharmaceuticals include various types of tablets, capsules, drinkable agents, etc. Optionally, the nutraceutical or pharmaceutical is suitable for topical application. Dosage forms can include, for example, capsules, oils, granula, granula subtilae, pulveres, tabellae, pilulae, trochisci, or the like.

The oil or lipids produced according to the methods described herein can be incorporated into products as described herein in combination with any of a variety of other agents. For instance, such compounds can be combined with one or more binders or fillers, chelating agents, pigments, salts, surfactants, moisturizers, viscosity modifiers, thickeners, emollients, fragrances, preservatives, etc., or any combination thereof.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

As used throughout, ranges (e.g., 1-10) and references to about a given value (e.g., about 1 or about 10) includes the recited value or values (e.g., 1 and/or 10)

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

Example 1. Repeated Fed-Batch Fermentation for Production of Biomass and Oil

In the field of microbial oil production, heterotrophic (dark) fermentation is generally considered superior to autotrophic microbial cultivation in terms of process efficiency and product yield. However, it is often hindered by higher fixed capital cost (the cost of constructing a vessel-based fermentation plant is generally much higher than the capital cost of open-pond and raceway type cultivation systems). Using a repeated fed-batch production process, higher overall volumetric productivities can be obtained while lowering operating costs. This is achieved by minimizing turnaround time of the production vessel and minimizing energy usage associated with a seed train and sterilization of the production vessel. This means better utilization of fixed capital investments (fermenters and associated equipment) and higher annual production capacity. There is also a reduced capital investment as only an initial seed train is used.

Figure 2:
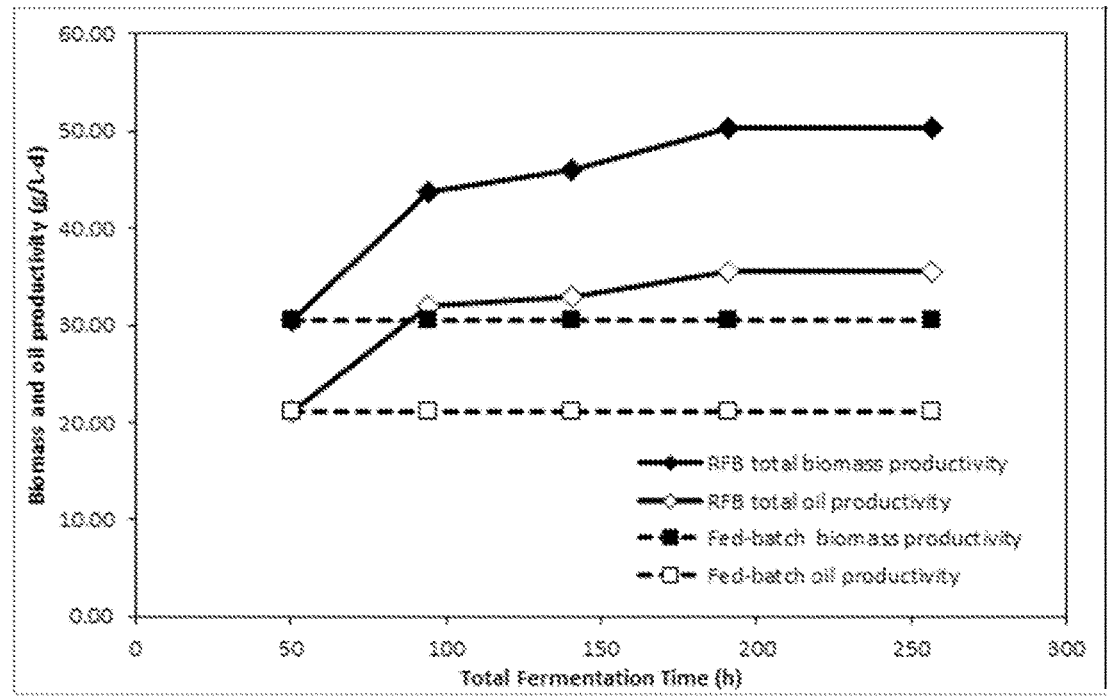
FIG. 2 is a graph showing biomass productivity and oil productivity improvement throughout a repeated fed-batch fermentation in 30 L fermenter, as well as constant biomass productivity and oil productivity of fed-batch fermentations. RFB in the legend stands for repeated fed-batch.

FIG. 1 shows the progression of in-vessel biomass concentration and oil concentration over time during a repeated fed-batch fermentation in a 30 L fermenter. For this experiment, 10% residual volume was employed using glucose as carbon source. In FIG. 2, a batch to batch turnaround time of 12 hours was used to calculate productivities of each independent fed-batch operation, and the same 12 hours turnaround time was used to calculate the first batch of the repeated fed-batch operation. As seen in FIG. 2, biomass and oil productivities of a typical fed-batch process will remain constant over time, because each subsequent fed-batch process is independently operated from the previous batch with a fixed turnaround time built in-between each fed-batch process. Conversely, after the first cycle of the repeated fed-batch process average productivity increases, far exceeding that of the fed-batch process as turnaround time is not required, and cycle time is decreased due to increased seed density.

Figure 3:
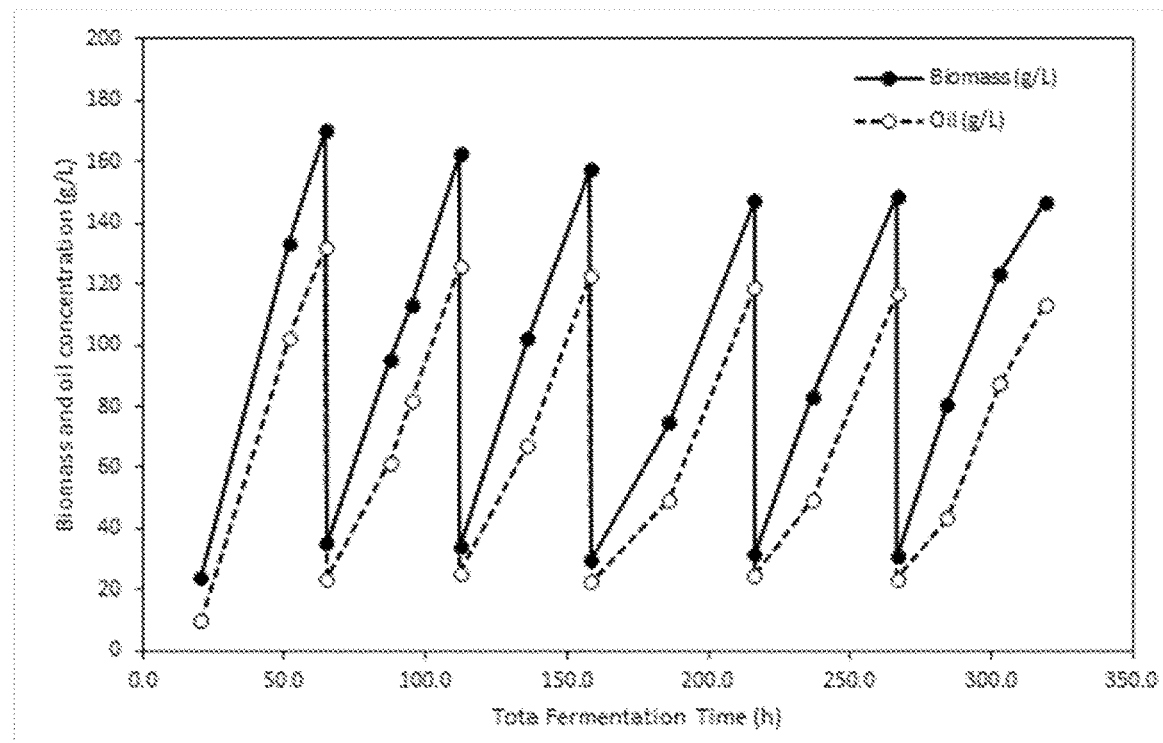
FIG. 3 is a graph showing the progression of in-vessel biomass concentration and oil concentration over time during a repeated fed-batch fermentation in a 7 L fermenter.
Figure 4:
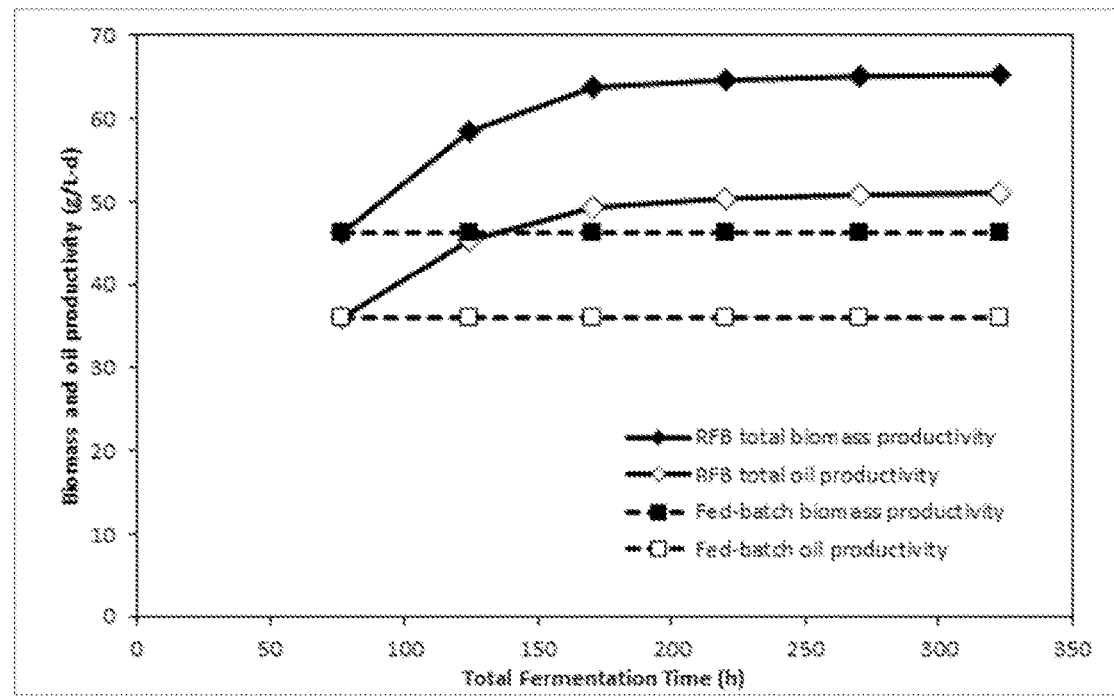
FIG. 4 is a graph showing biomass productivity and oil productivity improvement throughout a repeated fed-batch fermentation in 7 L fermenter, as well as constant biomass productivity and oil productivity of fed-batch fermentations. RFB in the legend stands for repeated fed-batch.

FIG. 3 shows the progression of in-vessel biomass concentration and oil concentration over time during a repeated fed-batch fermentation in a 7 L fermenter. For this experiment, 20% residual volume was employed using glucose as carbon source. In FIG. 4, a batch to batch turnaround time of 12 hours was used to calculate productivities of each independent fed-batch operation, and the same 12 hours turnaround time was used to calculate the first batch of the repeated fed-batch operation. As seen in FIG. 4, biomass and oil productivities of a typical fed-batch process will remain constant over time, because each subsequent fed-batch process is independently operated from previous batch with fixed turnaround time built in-between. Conversely, after the first cycle of the repeated fed-batch process average productivity increases, far exceeding that of the fed-batch process as turnaround time is not required, and cycle time is decreased due to increased seed density.

Figure 5:
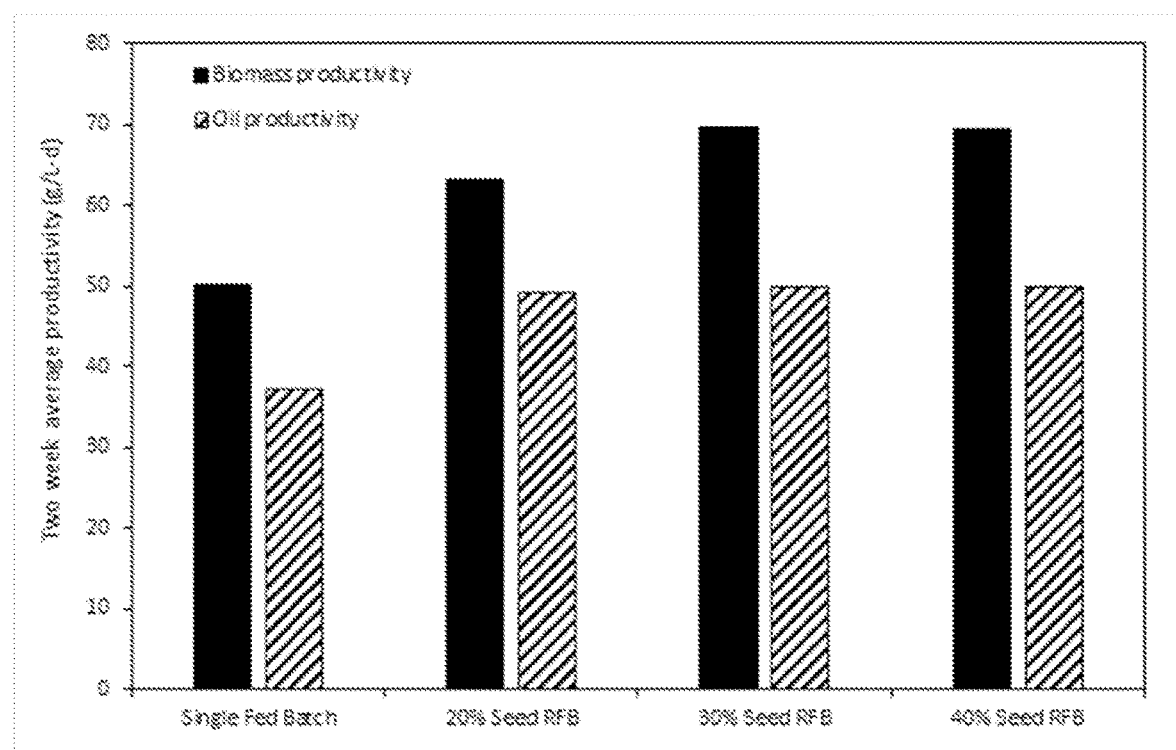
FIG. 5 is a graph showing the impact of changing residual seed volume (20%, 30%, and 40%) on the overall averaged biomass and oil productivities. RFB in the axis stands for repeated fed-batch.

Repeated fed-batch fermentations with different residual seed volumes, i.e., 20%, 30%, and 40%, were carried out over a period of 320 hours, each reaching total of six repeated operations. As seen in FIG. 5, all repeated fed-batch fermentations generated higher overall averaged biomass and oil productivities when compared to those of single fed-batch operation. Increasing residual seed volume from 20% to 30% resulted in significant increase in averaged productivities; while a further increase in residual seed volume from 30% to 40% brought no further productivity improvement. This showed the tradeoff between biomass left un-harvested (i.e. used as residual volume for seed), and reduced time spent in the lag-phase of the subsequent fermentation. Under these conditions, the optimum tradeoff point is approximately 30% residual seed volume.

What is claimed is:

1. A repeated fed batch method of culturing microorganisms comprising
   a. a cycle of steps comprising:
      (1) providing a container comprising one or more microorganisms and medium, wherein the microorganisms and medium form a start volume;
      (2) culturing the microorganisms in the medium in the container by a fed-batch method comprising:
         (a) culturing the microorganisms under conditions that favor biomass production; and
         (b) culturing the microorganisms of step (2)(a) under conditions that favor lipid production until the culture completes fermentation, and reaches a threshold volume when fermentation is complete, wherein the threshold volume is greater than the start volume and wherein the culturing comprises feeding one or more carbon sources to the culture;
      (3) harvesting a portion of the threshold volume of the culture from the container to leave a residual volume in the container that is 20% to 40% of the start volume;
      (4) adding fresh medium to the container in an amount to return the volume of the culture to the start volume; and
   b. repeating the cycle of steps one or more times,
   wherein the microorganisms are microalgae.

2. The method of claim 1, further comprising detecting during step (2)(b) volume of the culture, optical density (OD), dissolved oxygen (DO), cell concentration, carbon dioxide production rate, pH, time, concentration of nutrient in culture medium, biomass productivity, oil productivity, or any combination thereof.

3. The method of claim 2, wherein concentration of nutrient in the culture medium is detected and wherein the nutrient is carbon or nitrogen.

4. The method of claim 2, wherein volume of the culture is detected.

5. The method of claim 2, wherein cell concentration is detected.

6. The method of claim 1, comprising repeating the steps of (2), (3), and (4).

7. The method of claim 1, wherein the cycle of steps are repeated two or more times.

8. The method of claim 7, wherein the cycle of steps is repeated 2, 3, 4, 5, 6, 7, 8, 9, or 10 times.

9. The method of claim 1, wherein the lipids comprise triglycerides comprising fatty acids selected from the group consisting of alpha linolenic acid, arachidonic acid, docosahexaenoic acid, docosapentaenoic acid, eicosapentaenoic acid, gamma-linolenic acid, linoleic acid, linolenic acid, and combinations thereof.

10. The method of claim 1, wherein the lipids comprise triglycerides.

11. The method of claim 1, wherein the lipids comprise triglycerides comprising fatty acids selected from the group consisting of palmitic acid (C16:0), myristic acid (C14:0), palmitoleic acid (C16:1(n-7)), cis-vaccenic acid (C18:1(n-7)), docosapentaenoic acid (C22:5(n-6)), docosahexaenoic acid (C22:6(n-3)), and combinations thereof.

12. The method of claim 1, wherein the microorganism is a *Thraustochytrid*.

13. The method of claim 12, wherein the *Thraustochytrid* microorganism is of the family Thraustochytriaceae.

14. The method of claim 13, wherein the Thraustochytriaceae microorganism is of the genus *Thraustochytrium*.

15. The method of claim 14, wherein the Thraustochytriaceae microorganism is a microorganism deposited under ATCC Accession Number PTA-6245.

16. The method of claim 1, wherein oil productivity is determined.

17. The method of claim 1, wherein the residual volume comprises oil-rich cells.

18. A method of producing oil from a culture of oil-producing microorganisms comprising
   a. culturing the microorganisms according to the method of claim 1, and
   b. isolating oil from the harvested portion of the threshold volume.

19. The method of claim 1, wherein the method results in an oil productivity from 40 to 50 g/L/d.

20. The method of claim 1, wherein the method results in a biomass productivity from 50 to 70 g/L/d.

21. The method of claim 1, wherein oil productivity increases after each cycle.

22. The method of claim 1, wherein biomass productivity increases after each cycle.

* * * * *